(12) United States Patent
Dietrich et al.

(10) Patent No.: US 9,304,271 B2
(45) Date of Patent: Apr. 5, 2016

(54) CONNECTING ELEMENT FOR CONNECTING A FIBER-OPTIC LIGHT GUIDE TO A LIGHT SOURCE ONE TIME AND DETACHING THE FIBER-OPTIC LIGHT GUIDE FROM A LIGHT SOURCE ONE TIME

(71) Applicant: SCHOTT AG, Mainz (DE)

(72) Inventors: Andreas Dietrich, Guldental (DE); Thomas Reichert, Wackernheim (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 14/473,317

(22) Filed: Aug. 29, 2014

(65) Prior Publication Data
US 2014/0369655 A1 Dec. 18, 2014

Related U.S. Application Data

(63) Continuation of application No. PCT/EP2013/054027, filed on Feb. 28, 2013.

(60) Provisional application No. 61/604,669, filed on Feb. 29, 2012.

(30) Foreign Application Priority Data

Feb. 29, 2012 (DE) .......... 10 2012 203 118

(51) Int. Cl.
*G02B 6/42* (2006.01)
*A61B 18/20* (2006.01)
(Continued)

(52) U.S. Cl.
CPC .......... *G02B 6/4292* (2013.01); *A61B 1/00126* (2013.01); *A61B 1/00165* (2013.01);
(Continued)

(58) Field of Classification Search
CPC ...... A61B 18/20; A61B 18/201; A61B 18/22; A61B 1/00165; A61B 2018/00172; A61B 2018/00553; A61B 2018/2238; A61B 2019/4873; A61N 5/0601; A61N 2005/0644; A61N 5/0603; G02B 27/0994; G02B 6/3831; G02B 6/3849; G02B 6/3887; G02B 6/3893; G02B 6/4256; A61C 17/20; A61C 19/004; A61C 19/06
USPC .......... 385/92; D24/172; 606/13, 15
See application file for complete search history.

(56) References Cited

U.S. PATENT DOCUMENTS 4,763,663 A * 8/1988 Uphold et al. ......... 600/484
4,787,706 A * 11/1988 Cannon et al. ......... 385/59
(Continued)

FOREIGN PATENT DOCUMENTS

DE 4208844 A1 9/1993
DE 10245140 A1 4/2004
(Continued)

OTHER PUBLICATIONS

English translation of International Search Report dated Feb. 19, 2014 for corresponding International Application No. PCT/EP2013/054027, 3 pages.
(Continued)

*Primary Examiner* — Peter Radkowski
(74) *Attorney, Agent, or Firm* — Ohlandt, Greeley, Ruggiero & Perle, LLP

(57) ABSTRACT

A connecting element for connecting a fiber-optic light guide to a light source one time and detaching the fiber-optic light guide from a light source one time is provided. The connecting element includes a housing having a wall, where the housing encloses a cavity, a fiber-optic light guide that passes through the housing and the cavity, a connecting piece corresponding to a connecting section of the light source for establishing the connection to the light source, where the connecting section can be reused after the detachment, and prevention device configured to prevent repeated use of the connecting element and/or the light guide.

17 Claims, 9 Drawing Sheets

(51) Int. Cl.
*A61B 1/00* (2006.01)
*F21V 8/00* (2006.01)
*A61B 18/00* (2006.01)
*A61B 19/00* (2006.01)
*A61N 5/06* (2006.01)

(52) U.S. Cl.
CPC ............. *A61B18/20* (2013.01); *G02B 6/4256* (2013.01); *A61B 18/201* (2013.01); *A61B 2018/00172* (2013.01); *A61B 2018/00553* (2013.01); *A61B 2019/4873* (2013.01); *A61N 5/062* (2013.01); *G02B 6/0006* (2013.01); *G02B 6/4298* (2013.01)

(56) References Cited

U.S. PATENT DOCUMENTS

| | | | | |
|---|---|---|---|---|
| 5,104,378 | A * | 4/1992 | Haber et al. | 604/110 |
| 5,197,487 | A * | 3/1993 | Ackerman et al. | 600/589 |
| 5,334,019 | A * | 8/1994 | Goldsmith et al. | 433/88 |
| 5,573,510 | A * | 11/1996 | Isaacson | 604/158 |
| 5,573,533 | A * | 11/1996 | Strul | 606/34 |
| 5,752,829 | A * | 5/1998 | Goldsmith et al. | 433/88 |
| 5,798,518 | A * | 8/1998 | Coleman et al. | 250/205 |
| 6,056,726 | A * | 5/2000 | Isaacson | 604/164.01 |
| 6,193,690 | B1 * | 2/2001 | Dysarz | 604/161 |
| 6,764,485 | B2 * | 7/2004 | Hareyama et al. | 606/11 |
| 6,826,422 | B1 * | 11/2004 | Modell et al. | 600/407 |
| 6,994,690 | B2 * | 2/2006 | Kiehne | 604/110 |
| 7,171,265 | B2 * | 1/2007 | Hoium et al. | 607/2 |
| 7,610,091 | B2 * | 10/2009 | Hoium et al. | 607/27 |
| 7,766,874 | B2 * | 8/2010 | Liniger | 604/164.01 |
| 7,828,768 | B2 * | 11/2010 | Chen | 604/110 |
| 8,075,523 | B2 * | 12/2011 | Wayman et al. | 604/110 |
| 8,235,975 | B2 * | 8/2012 | Chen et al. | 606/14 |
| 8,388,523 | B2 * | 3/2013 | Vivenzio et al. | 600/178 |
| 8,416,291 | B2 * | 4/2013 | Carrey et al. | 348/77 |
| 8,551,088 | B2 * | 10/2013 | Falkenstein et al. | 606/51 |
| 8,562,598 | B2 * | 10/2013 | Falkenstein et al. | 606/33 |
| 8,568,411 | B2 * | 10/2013 | Falkenstein et al. | 606/51 |
| 8,579,894 | B2 * | 11/2013 | Falkenstein et al. | 606/45 |
| 8,915,910 | B2 * | 12/2014 | Falkenstein et al. | 606/34 |
| 2002/0045243 | A1 * | 4/2002 | Laska et al. | 435/287.1 |
| 2002/0128685 | A1 * | 9/2002 | Hoium et al. | 607/1 |
| 2002/0193736 | A1 * | 12/2002 | Kiehne | 604/110 |
| 2003/0065315 | A1 * | 4/2003 | Hareyama et al. | 606/11 |
| 2004/0116857 | A1 * | 6/2004 | Kiehne | 604/110 |
| 2004/0186382 | A1 * | 9/2004 | Modell et al. | 600/473 |
| 2004/0267340 | A1 * | 12/2004 | Cioanta et al. | 607/105 |
| 2005/0113814 | A1 * | 5/2005 | Loeb | 606/15 |
| 2005/0113815 | A1 * | 5/2005 | Ritchie et al. | 606/15 |
| 2005/0228345 | A1 * | 10/2005 | Yang et al. | 604/110 |
| 2006/0200080 | A1 * | 9/2006 | Abulhaj | 604/164.01 |
| 2007/0093871 | A1 * | 4/2007 | Hoium et al. | 607/2 |
| 2007/0112303 | A1 * | 5/2007 | Liniger | 604/164.01 |
| 2007/0260231 | A1 * | 11/2007 | Rose et al. | 606/13 |
| 2008/0096167 | A1 * | 4/2008 | Florman | 433/166 |
| 2008/0255549 | A1 * | 10/2008 | Rose et al. | 606/15 |
| 2009/0248007 | A1 * | 10/2009 | Falkenstein et al. | 606/33 |
| 2009/0248013 | A1 * | 10/2009 | Falkenstein et al. | 606/41 |
| 2009/0248019 | A1 * | 10/2009 | Falkenstein et al. | 606/42 |
| 2009/0248020 | A1 * | 10/2009 | Falkenstein et al. | 606/45 |
| 2009/0248022 | A1 * | 10/2009 | Falkenstein et al. | 606/51 |
| 2009/0259193 | A1 * | 10/2009 | Chen | 604/192 |
| 2009/0287192 | A1 * | 11/2009 | Vivenzio et al. | 606/1 |
| 2009/0322867 | A1 * | 12/2009 | Carrey et al. | 348/77 |
| 2010/0274190 | A1 * | 10/2010 | Wayman et al. | 604/110 |
| 2011/0015573 | A1 * | 1/2011 | Maan et al. | 604/110 |
| 2011/0144630 | A1 * | 6/2011 | Loeb | 606/16 |
| 2011/0184239 | A1 * | 7/2011 | Wright et al. | 600/118 |
| 2012/0089207 | A1 * | 4/2012 | Chen et al. | 607/92 |
| 2014/0066927 | A1 * | 3/2014 | Brustad et al. | 606/41 |

FOREIGN PATENT DOCUMENTS

| | | | | |
|---|---|---|---|---|
| EP | 0467631 | A2 | 1/1992 | |
| EP | 0476024 | A1 | 3/1992 | |
| JP | 2005185829 | A * | 7/2005 | A61B 18/20 |

OTHER PUBLICATIONS

English translation of Written Opinion of the International Searching Authority dated Feb. 19, 2014 for corresponding International Application No. PCT/EP2013/054027, 14 pages.

English translation of International Preliminary Report on Patentability dated Sep. 2, 2014 for corresponding International Application No. PCT/EP2013/054027, 15 pages.

* cited by examiner

CONNECTING ELEMENT FOR CONNECTING A FIBER-OPTIC LIGHT GUIDE TO A LIGHT SOURCE ONE TIME AND DETACHING THE FIBER-OPTIC LIGHT GUIDE FROM A LIGHT SOURCE ONE TIME

CROSS REFERENCE TO RELATED APPLICATIONS

This application is a continuation International Application No. PCT/EP2013/054027, filed Feb. 28, 2013, which claims the benefit of U.S. Provisional Application Ser. No. 61/604,669, filed Feb. 29, 2012 and claims benefit under 35 U.S.C. §119(a) of German Patent Application No. 10 2012 203 118.9, filed Feb. 29, 2012, the entire contents of all of which are incorporated herein by reference.

BACKGROUND

1. Field of the Disclosure

The present invention relates to a connecting element for connecting a fiber-optic light guide to a light source one time and detaching the fiber-optic light guide from a light source one time. In this context, light source shall be understood not only as the light source itself, but also the components necessary for coupling of light or other radiation in the light guide. With the use of the terms light guide and light source, there is no limitation of the application of the present invention just to visible light.

2. Description of Related Art

Applications in which the light guide is used for endoscopic treatments, for example, for sclerothearpy of hemorrhoids in the human body, are emphasized. For this purpose, the light source produces IR radiation, which is coupled in the light guide and is directed via the light guide to the site where the hemorrhoids are found. Based on the endoscopic use of the light guide, it must be assured that it is sterile. Consequently, after terminating treatment, the question arises as to how to proceed further with the used light guide. Basically, the light guide could be cleaned and sterilized after use, for example, by means of UV radiation or by autoclaving. Several aspects must be noted here, however: In a physician's practice or in a hospital, where the corresponding treatment is usually conducted, a cleaning by means of appropriate cleaning agents and a sterilization by means of UV radiation or other means in general cannot be practically conducted. In this case, sterilization by means of an autoclave is more suitable, whereby it must be observed that autoclavable plastics must be utilized, which, however, are in general relatively expensive to acquire and thus make the light guide more expensive. Appropriate cleaning devices and autoclaves are not generally available on the market.

In all sterilization procedures that are conducted after the use of the light guide mentioned here, the risk always remains that the sterilization has not been carried out to the extent necessary. There remains a specific residual risk of an infection of the patient who is treated with a light guide that has already been used. Consequently, it is expedient to use such a light guide only once and to discard it after use. However, it must be assured that an unused light guide is actually utilized in such cases. For this purpose, the use of a connecting element with which the unused fiber-optic light guide can be connected only once with the component, particularly the light source, and can be detached also only once, is offered.

Screw connections, which can be used only once are known from the prior art. A one-time screw connection for an airbag is disclosed in DE 42 08 844, with which two components can be screwed together, but can only be detached again from one another by being destroyed. Both the screw as the connecting element and the thread as corresponding connecting segment can no longer be used after detaching. Such a connection, however, is not appropriate in the present case of application, since the light source and the corresponding connecting segment, usually disposed in the housing of the light source, are to be used again with another, new light guide.

US 2008/0255549 describes a light guide, which can be connected to a light source by means of clips. The light guide can be designed as a disposable product for reasons of sterility. The clips are destroyed upon detaching the light guide, so that any further use is excluded.

DE 102 45 140 discloses a light guide that has a transponder, on which different data can be stored, for example, the number of treatments. As long as the light guide is designed as a light guide for one-time use, a warning tone can be generated if the light guide is about to be used a second time.

SUMMARY

The object of the present invention is thus to create a connecting element for the one-time connection and the one-time detachment of the fiber-optic light guide with a corresponding connecting segment, which assures that only new, unused, fiber-optic light guides can be used in a functionally correct manner, but without destroying the connecting segment.

The object is achieved with a connecting element of the type named initially, which comprises a housing with a wall structure that encloses a cavity, a fiber-optic light guide passing through the housing and the cavity, and a connecting piece corresponding to a connecting segment of the light source for producing the connection to the light source. In this case, the connecting piece is disposed at least partially in the cavity of the housing and is movable relative to the housing as a function of one or more events, whereby the connecting segment can be used again after detaching. In addition, the connecting element comprises means for preventing a repeated functionally correct use of the connecting element and/or of the light guide based on one or more selectable events. Functionally correct use shall be understood to mean that, on the one hand, the connecting element is able to produce a connection with the light source, and, on the other hand, the light guide can guide light or radiation to its distal end facing away from the light source, whereby in the case of functionally correct use, an optimal light coupling is also assured with correspondingly optimized distance between light coupling surface and light source, as well as an optimal irradiation with respect to an incidence angle and a numerical aperture (NA) of the fiber. With the first use of the connecting element, the fiber-optic light guide is connected by means of the connecting piece to the corresponding connecting segment, which is found, for example, in the housing of the light source. Subsequently, the treatment, for example, the sclerotherapy of hemorrhoids, is conducted by guiding the IR radiation produced by the light source through the light guide to the site to be treated in the human body. After terminating the treatment, the fiber-optic light guide and the connecting element are separated from the light source. The means provide that the connecting element and/or the light guide can no longer be used in a functionally correct manner. If the connection means is no longer fully functional, then a connection with the light source can no longer be produced and/or an optimal light coupling cannot be assured. The latter is expressed by a clear decrease in efficiency. On the other hand, if the light guide is destroyed or at least partially damaged, then radiation can no longer be brought to the site of the human body to be treated. In this case, it is in fact conceivable that the connection to the light source can still be produced; however, modern light sources that are used for the sclerotherapy of hemorrhoids have control devices that communicate to the treating physician immediately when no radiation dose or an insufficient dose arrives at the distal end of the light guide, so that another, unused light guide must be used. In both cases, it is thus assured that an already used light guide is not used a second time. The selectable events in this case can be physical and/or chemical effects, as will be described further below.

Preferably, the selectable event is a movement of the housing relative to the connecting segment when the connecting element is connected to the light source or when it is detached from the light source. When the connecting element is connected and/or detached, the connecting element interacts with the connecting segment of the light source. Forces or torques are induced thereby, which activate the means so that the light guide and/or the connecting element cannot be used a second time in a functionally correct manner. The use of the movement of the housing as a selectable event has the advantage that complicated measures need not be employed in order to activate the means. In addition, this embodiment represents a very reliable way for activating, since connecting and detaching the connecting element presuppose a movement of the housing that cannot be avoided.

A preferred embodiment is characterized in that the connecting piece is movable between a first end position and a second end position, whereby the connecting piece in the first end position projects out from the housing, while it is disposed completely or nearly completely in the cavity in the second end position, and that the means comprise a pre-stressing element that pre-stresses the connecting piece in the first end position, and a retaining element that holds the connecting piece in the first end position and releases it based on the movement of the housing, so that the connecting piece is moved into the second end position by the pre-stressing element. This embodiment can be simply manufactured from a technical manufacturing viewpoint and is characterized by a high reliability. In the first end position, the connecting piece projects out from the housing and thus can be connected to the corresponding connecting segment of the light source. As a consequence of the movement of the housing when connecting or detaching, forces and/or torque enter(s) into the connecting element, which induces the retaining element to release the connecting piece. Based on the restoring force of the pre-stressing element, subsequently, the connecting piece is moved into the second position, in which it no longer projects from the housing or only a small part of it projects. If the connecting piece no longer projects from the housing out beyond the housing, it is no longer possible to connect the connecting element or the connecting piece to the corresponding connecting segment. If it projects only partially over the housing, then the light guide can no longer be introduced sufficiently close to the light source, so that the radiation can no longer be coupled in the light guide to a sufficient extent. In both cases, the light guide can no longer be used in a functionally correct manner. It is also no longer possible to reintroduce the connecting piece into the first end position without tools and without destroying the connecting element. In this way, it is prevented that the used light guide is employed a second time.

Preferably, the selectable event is a rotational movement of the housing relative to the connecting piece. In many cases, the connection between two components is provided by means of a screw connection. This type of connection is also offered in this case. Thus, the housing is rotated for connecting and for detaching. The retaining element can be designed here so that when screwing in takes place, it is triggered starting from a certain torque. The light guide or the connecting piece is still not moved into the second end position thereby, since the corresponding connecting segment of the light source holds the connecting piece in the first position. However, as soon as the connecting piece is completely removed from the connecting segment of the light source, a retaining force no longer acts on the connecting piece, so that it is moved into the second end position.

Preferably, the retaining element comprises a projection which runs in a recess having a blocking segment. In this case, the recess preferably runs in the wall structure of the housing and makes possible the movement of the connecting piece between the first end position and the second end position. Here, the cavity is essentially cylindrical, so that the connecting piece executes a movement along the longitudinal axis of the cavity between the first and the second end positions. Further, the connecting piece is mounted rotatably in the cavity. The blocking segment is formed here by a radial expansion of the recess. The blocking segment has a clearly smaller axial extension than the rest of the recess. In the factory, the projection is introduced into the blocking segment. The closed end of the blocking segment lying in the direction of action of the pre-stressing element defines the first end position, against which the projection is pressed. When the connecting piece is screwed into the corresponding connecting segment by rotating the housing, the projection is pressed against the closed side wall of the blocking segment, so that a relative movement between the connecting piece and the housing is not possible. When detaching, the housing is rotated in the opposite direction, so that the projection is guided out of the blocking segment by a relative movement between the connecting piece and the housing, so that an axial movement within the remaining recess to the second end position can result. In the second end position, the relative movement between the housing and the connecting piece is prevented again by the side walls of the remaining recess. This embodiment is particularly simple to manufacture and is characterized by a high reliability.

Another embodiment is characterized by the fact that the selectable event is a translational movement of the housing relative to the connecting piece, by means of which the retaining element releases the connecting piece. Instead of a screw connection, a plug connection can also be provided, in which the connecting piece is designed as a plug, which is inserted into the corresponding connecting segment. In order to assure a secure seating in the connecting segment, the connecting piece is provided with a certain over-dimensioning or spring-action elements are provided in the corresponding connecting segment. Now, if the connecting element is to be separated from the light source, a certain force must be introduced on the housing along the longitudinal axis. This force can be used for the purpose of releasing the retaining element. This can be accomplished, for example, in that the housing comprises an outer casing that can move axially relative to the rest of the housing; this casing must be grasped by the user in order to detach the connecting element. The retaining element is released due to the axial relative movement of the casing with respect to the rest of the housing. This embodiment also can be simply manufactured from a technical manufacturing viewpoint and is characterized by a high reliability.

An enhancement of the connecting element according to the invention has a restraining element for holding the connecting piece in the second end position. This can be a catch piece, which releases the passage of the connecting piece into the second end position, but then holds the connecting piece solidly in the second end position, so that it can no longer be moved into the first end position. In this way, it is prevented or at least clearly made difficult for the connecting piece to be able to be introduced back into the first end position by means of manipulation with the use of tools.

Preferably, the means are aligned so that with a relative movement between the connecting piece and the housing, the fiber-optic light guide is moved so that it falls below a permissible bending radius. The circumstance exploited here is that the fibers, which are used for the fiber-optic light guide, have a permissible bending radius, but, when the radius is below this, the fibers break and thus become unusable. The fiber-optic light guide is guided in this embodiment in such a way that in the initial state, in which the connecting element is connected to the light source, it passes through a radius that lies somewhat above the permissible bending radius. In this state, all of the coupled light is guided through the fiber-optic light guide. The relative movement between the connecting piece and the housing that is triggered when the connecting element is detached from the light source causes a reduction in the radius to a value below the permissible bending radius, so that least a majority of the fibers break. The movement can cause a compressing, shearing or crushing of the fibers. Consequently, only a small portion of the coupled light or coupled radiation can be conducted through the fiber-optic light guide. Modern equipment that is utilized for the sclerotherapy of hemorrhoids may have control devices that signal the treating physician immediately when no light or no IR radiation or an insufficient amount appears at the distal end. In this case, a clear indication is given to the treating physician that a new, unused light guide must be used. In this way the light guide can be made unusable in a simple way by the simply configured connecting element according to the invention.

In another embodiment of the connecting element according to the invention, the connecting piece has a thread, which expands radially upon a relative movement between the connecting piece and the housing. For this purpose, the thread can have elastic or pre-stressed sections that are held by a ring or by another suitable restraining means in a first position, in which it does not destroy the use of the thread. This restraining means can be destroyed by screwing into a counter-thread of the connecting segment of the light source, so that the means can no longer keep the elastic or pre-stressed sections in the first position. If the thread is removed from the connecting segment, the sections expand radially, so that the thread can no longer be screwed into the connecting segment. This embodiment is characterized by a particularly simple manufacture and a high reliability.

In another enhancement, the means comprise one or more cutting element(s) for at least partially cutting through the fiber-optic light guide. The cutting element can be actuated, for example, by a rotational or translational movement of the housing relative to a section interacting with the cutting element. In this case, it is no longer possible to use the light guide for the passage of light and in particular of IR radiation. Modern equipment that is utilized for the sclerotherapy of hemorrhoids may have control devices that signal the treating physician immediately when no light or no IR radiation appears any longer at the distal end. In this case, a clear indication is given to the treating physician that a new, unused light guide must be used. In this way, it is prevented that an already used light guide is employed again. A cutting element can also be implemented in a simple way from a technical manufacturing viewpoint and thus has a high reliability.

Another embodiment of the connecting element according to the invention is characterized in that the selectable event is the exceeding of a specific temperature. The light guide can be configured so that a part of the coupled radiation, for example, IR radiation, can exit the light guide at a definable section. If IR radiation is guided further via the light guide, the housing of the connecting element according to the invention also heats up and after a certain time exceeds a specific temperature. This heat, for example, can be used for the purpose of allowing the melting of the projection that holds the connecting piece in the first end position after the specific temperature is exceeded, so that the pre-stressing force of the pre-stressing element is no longer increased. Consequently, the projection can no longer hold the connecting piece in the first end position. For this purpose, the projection can be manufactured of a plastic that melts at the specific temperature.

In another enhancement of the present connecting element, the selectable event is the effect of a specific dose of radiation. As has already been mentioned, the light guide is preferably used for the transmission of IR radiation. Here, this radiation can also be directed partially onto the means for preventing a repeated functionally correct use of the connecting element and/or of the light guide, for which reason, the light guide can have definable sections through which a portion of the radiation can pass and impinge on these means. Thus, for example, the projection that holds the connecting piece in the first end position can be manufactured from a plastic that is displaced under the effect of a specific dose of radiation, so that the connecting piece is no longer held in the first end position and is moved into the second end position. In addition, it is conceivable that by means of a combination of exceeding a specific temperature and the effect of a specific radiation dose, a chemical reaction of a plastic is induced, which prevents the connecting element and/or the light guide from being able to be used a second time in a functionally correct manner.

In addition, it is conceivable to design the connecting element according to the invention so that several selectable events may occur, so that a redundancy is created. In this way, the danger that the connecting piece remains in the first position is reduced, although the connecting element has already been connected once to the component and has been detached from it. The operating safety is increased thereby and the probability that the fiber-optic light guide is used a second time is reduced.

In an enhancement, the fiber-optic light guide comprises quartz fibers, individual glass fibers, bundles of quartz or glass fibers, plastic light guides, and/or liquid light guides. Depending on which type of radiation is to be transmitted, specific embodiments of the light guide are more suitable than others. Liquid light guides are particularly suitable for the transmission of UV radiation, whereas plastic light guides, also called polymeric optical fibers, which are produced, for example, from polymethyl methacrylate (PMMA) are more favorable in production, in comparison to glass fibers.

Preferred examples of application are the sclerotherapy of hemorrhoids by means of IR radiation, laser eye treatment by means of IR lasers (e.g., neodymium-YAG laser, 1.06 μm), dental laser surgery, and photodynamic therapy (PDT).

Another aspect of the invention relates to the use of the connecting element according to one of the previously described embodiment examples for fiber-optic components in medical technology for the treatment of tissue surfaces or for surgical interventions by means of UV, VIS and/or IR radiation. In addition, the invention relates to the use of the connecting element according to the invention according to one of the previously described embodiment examples for catheters or flexible-tubing connections in the field of medical technology. The technical effects and advantages, which result from this use, correspond to those that have also been presented as such for the connecting element.

Another aspect of the invention relates to a connecting element for the one-time connection and one-time detachment of a line to or from a technical medical component or device, comprising a housing with a wall structure, which encloses a cavity, a line passing through the housing and the cavity, a connecting piece corresponding to a connecting segment of the technical medical component or device for producing the connection to the technical medical component or device, whereby the connecting segment can be used again after detaching, and means for preventing a repeated, functionally correct use of the connecting element and/or the line based on one or more selectable events. A flexible tubing can be considered as a line, which is used for the transporting of bodily fluids such as blood or urine. The connecting element according to the invention can be used, for example, in catheter systems or in dialysis devices where sterile flexible tubing must be connected to technical medical devices such as pumps, and a second use of the flexible tubing involves risks of infection and should be prevented. The technical effects and advantages that result from this use correspond to those that have been discussed previously.

BRIEF DESCRIPTION OF THE DRAWINGS

The invention will be explained in detail below based on preferred embodiment examples with reference to the appended drawings. Herein.

DETAILED DESCRIPTION

Figure 1:
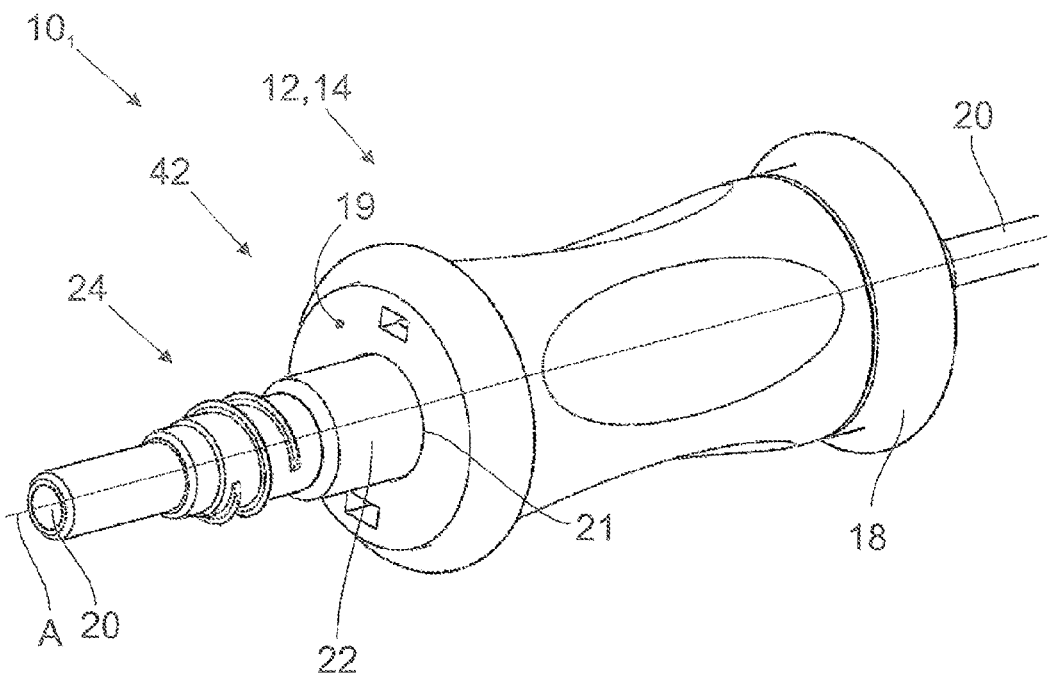
FIG. 1 shows a first example of embodiment of the connecting element according to the invention in a perspective view in a first end position.

A first example of embodiment of the connecting element $10_1$ according to the invention, which is based on a perspective view, is shown in FIG. 1. The connecting element $10_1$ comprises a housing 12 with a wall structure 14, which encloses a cavity 16, which is not visible here (see FIG. 3). The wall structure 14 comprises a cover 18, with which the cavity 16 can be opened and closed during manufacture. In the state when delivered, however, the cover 18 cannot be removed non-destructively from the housing 12. In addition, the wall structure 14 comprises a front wall 19 with an opening 21. A fiber-optic light guide 20 passes through the housing 12 along a longitudinal axis A. A portion of a connecting piece 22 projects from the opening 21 of the housing 12 beyond the front wall 19, the connecting-piece portion enclosing the fiber-optic light guide 20 and having a thread 24, whereas the remaining portion of the connecting piece 22 is disposed in the cavity 16 of the housing 12 and is mounted in a rotatable manner therein. The light guide 20 can be connected by this connecting piece 22 to a light source 26, which is not shown here, and which has for this purpose a connecting segment 28 corresponding to the connecting piece 22 (see FIG. 10). In the connected state, the connecting element $10_1$ is applied by its front surface 19 to the light source 26.

Figure 2:
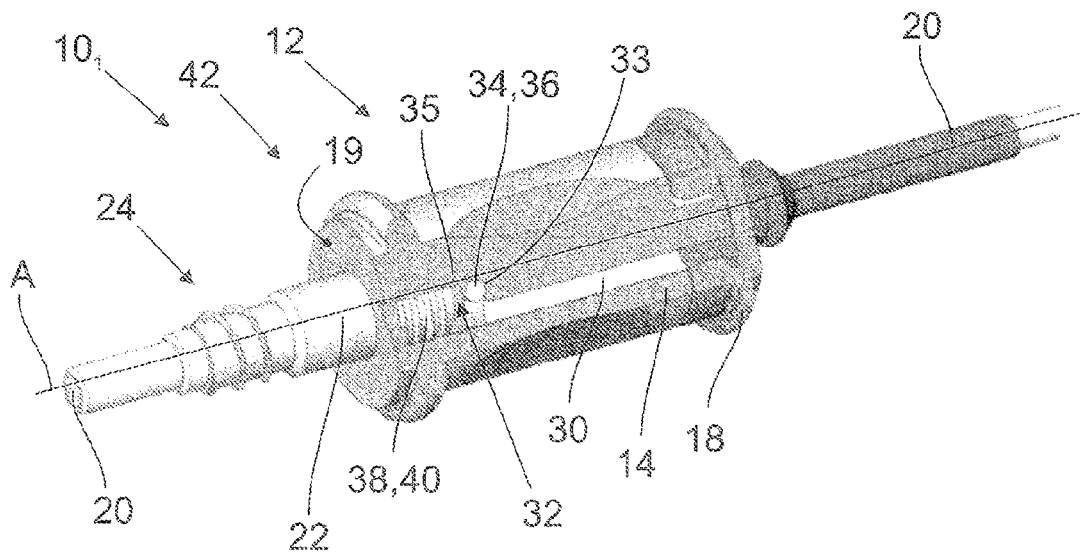
FIG. 2 shows the first example of embodiment also in a perspective sectional view, wherein the sectional plane does not run through the longitudinal axis, in a first end position.

The connecting element $10_1$ according to the invention, which is shown in FIG. 1, is shown again in FIG. 2, wherein the housing 12 is partially cut away. It is recognized that a recess 30 in the wall structure 14 runs essentially parallel to the longitudinal axis A, which has a blocking segment 32 that is formed by a radial expansion of the recess 30. The blocking segment 32 has a closed end 33, which is directed axially to the cover 18, and a closed side wall 35.

In addition, it can be recognized that the connecting piece 22 has a retaining element 34, in this case designed as a projection 36, which is found in the blocking segment 32. Further, a pre-stressing element 38, here designed as a spring 40, is visible, which is supported on one side against the wall structure 14, and on the other side against the connecting piece 22. The retaining element 34 and the connecting piece 22 belong to the means 42 for preventing a repeated functionally correct use of the connecting element 10 and/or of the light guide 20 based on one or more selectable events, as will be presented in more detail in the following.

The projection 36 abuts against the closed end 33 of the blocking segment 32 and holds the connecting piece 22 in the first end position, whereby the pre-stressing element 38 is pre-stressed.

Figure 3:
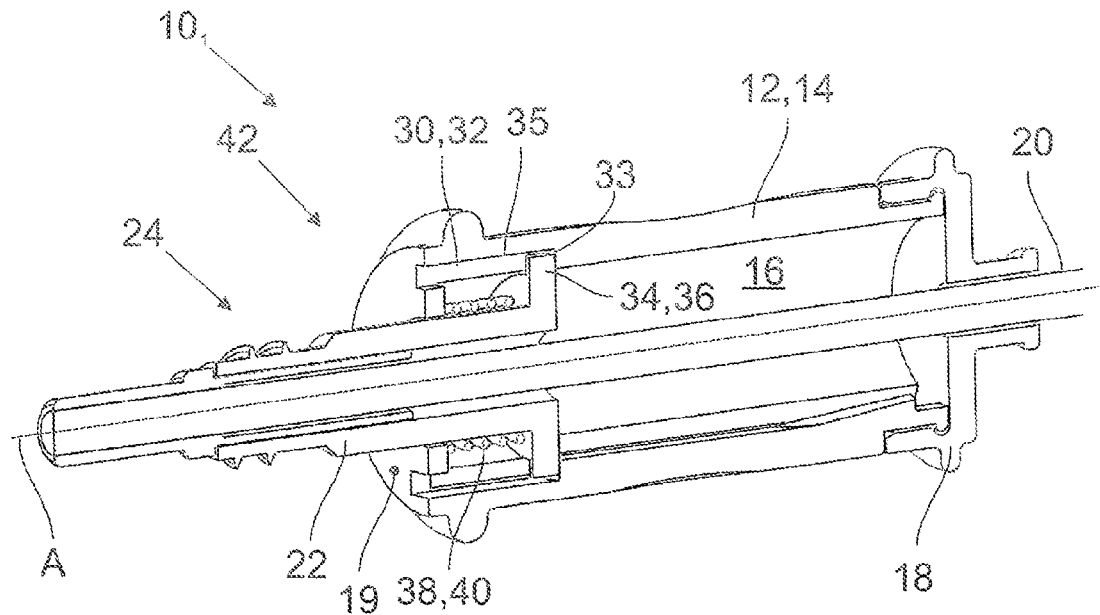
FIG. 3 shows the first example of embodiment in a perspective sectional view, wherein the sectional plane runs through the longitudinal axis, in a first end position.

The connecting element 10 according to the invention is shown perspectively in FIG. 3, based on a sectional view through the longitudinal axis A. Two projections 36 can be recognized, which are supported against the closed end 33 of the blocking segment 32.

Figure 4:
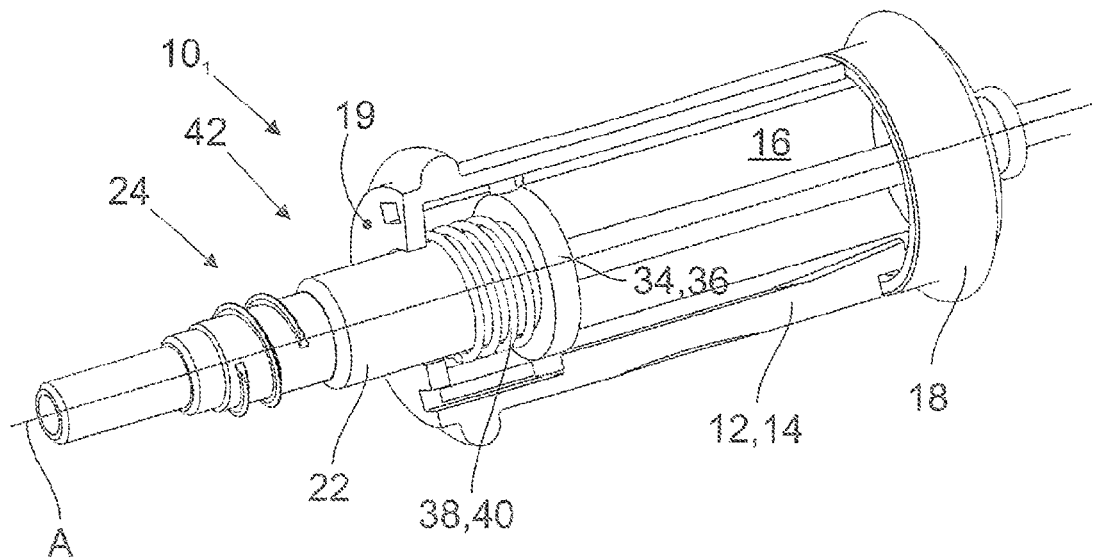
FIG. 4 shows the first example of embodiment also in a perspective representation, wherein the sectional plane runs through the longitudinal axis, but only a portion of the housing is cut away, in a first end position.

Only the housing 12 is cut away in FIG. 4. It can once more be recognized how the two projections 36 hold the connecting piece 22 in the first end position under compression of the spring 40.

Figure 5:
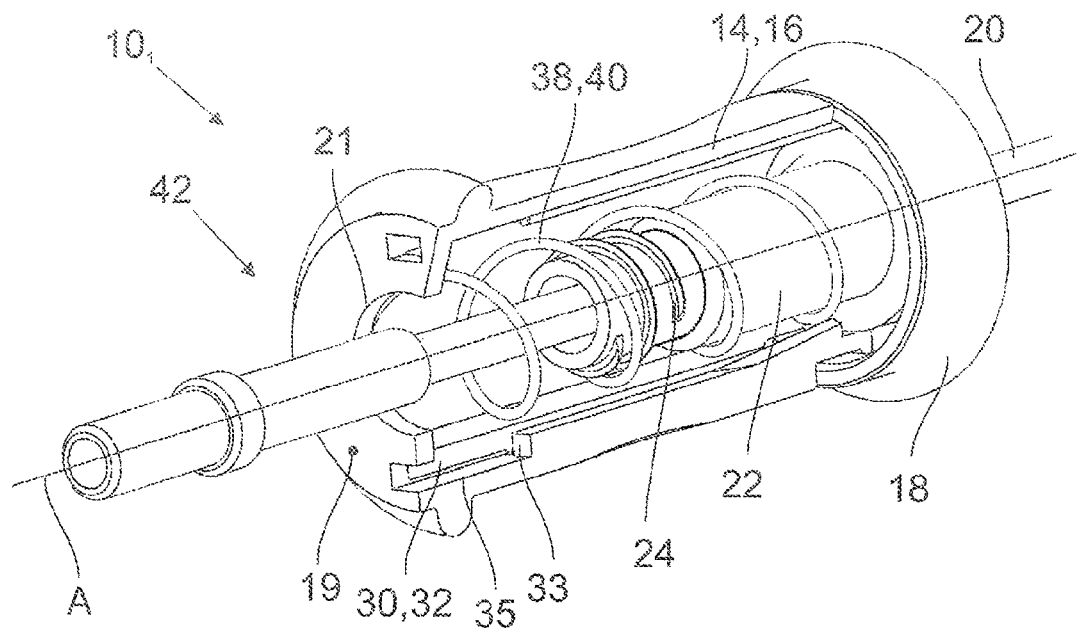
FIG. 5 shows the first example of embodiment in a perspective sectional view, wherein only a portion of the housing is cut away, in a second end position.

The connecting element 10 according to the invention is shown in a second end position in FIG. 5. It can be recognized that only the light guide 20 still projects beyond the front surface 19 of the housing 12, but not the connecting piece 22, which has been moved by means of the pre-stressing element 38 into the second end position and is now found completely in the cavity 16. The position of the light guide 20, however, has not been changed, since in the first example of embodiment, the connecting piece 22 is disposed so that it can be moved onto the light guide 20.

The movement of the connecting piece 22 from the first into the second end position is carried out in the following way: In the initial state, the projection 36 is found in the blocking segment 32 of the recess 30 and lies against the closed end 33. The connecting piece 22 is thus held in the first end position by the pre-stressing of the pre-stressing element 38. The thread 24 specifies one direction of rotation, in which the connecting element 10 must be rotated in order to screw it into the corresponding connecting segment 28 of the light source 26. The blocking segment 32 is configured so that the projection 36 is pressed on the closed side wall 35 of the blocking segment 32 when it is screwed in, and thus remains in the blocking segment 32. If the housing 12 is rotated in the direction of screwing in, the projection entrains the connecting piece 22, so that there is no relative movement between the housing 12 and the connecting piece 22. In order to prevent an unintentional detachment of the projection 36 from the blocking segment 32, the closed end 33 may have a shape corresponding to the projection 36. When detaching, the connecting element 10 must be rotated in the opposite direction, whereby the projection 36 is removed from the closed end 33 and is brought from the blocking segment 32 into the remaining region of the recess 30. In this case, a relative movement occurs between the connecting piece 22 mounted in a rotatable manner and the housing 12. At the beginning of the rotation for detaching, the thread 24 is still found in the connecting segment 28, so that the connecting piece 22 is fixed axially and is held in the first end position. The projection 36 bumps up against the end of the recess 30 that lies radially opposite the blocking segment 32, so that the connecting piece 22 is rotated together with the housing 12, and a relative movement between the housing 12 and the connecting piece 22 is not possible. As soon as the thread 24 has been removed from the connecting segment 28, the axial fixation of the connecting piece 22 in the first end position is discontinued and the connecting piece 22 is moved into the second end position. The connecting piece 22 is now found completely in the cavity 16 and cannot interact with the corresponding connecting segment 28 of the light source 26, so that a connection with the light source 26 can no longer be produced. It is not absolutely necessary, however, that the connecting piece 22 in the second end position is completely located in the cavity 16. A small piece can also protrude from the housing 12, of course, only to such a small extent that either a retaining connection can no longer be produced relative to the light source 26 or radiation can no longer be sufficiently coupled in the light guide 20 in order to provide at the distal end a radiation dose that is sufficient for the respective purpose of application.

Figure 6:
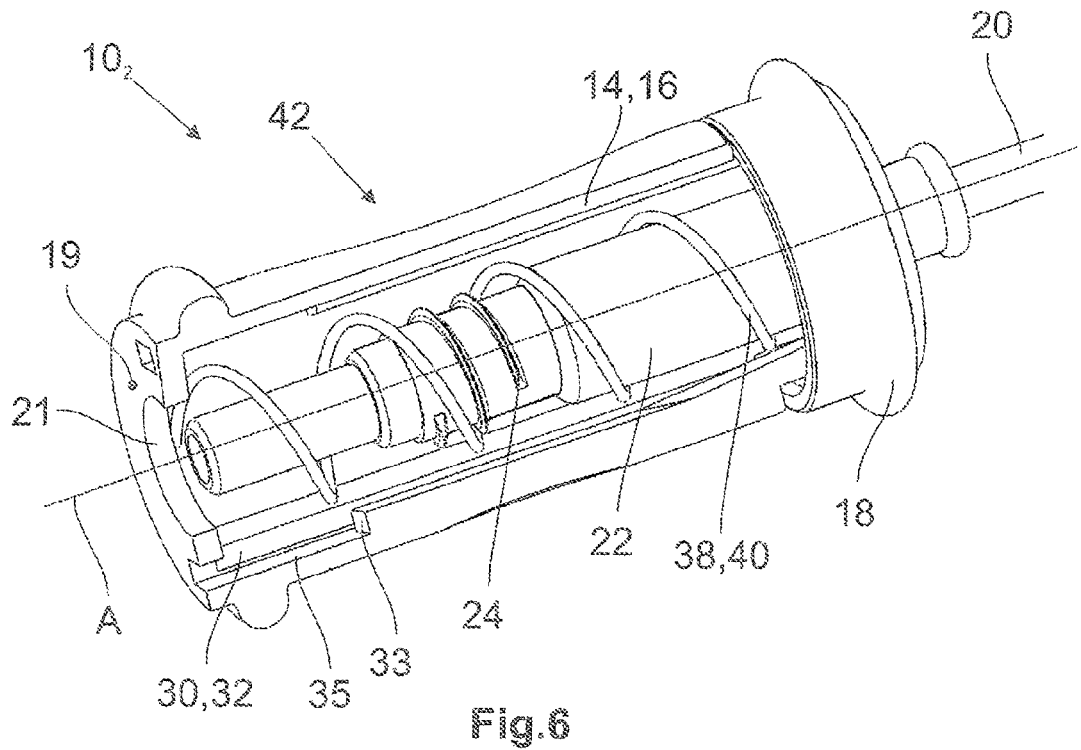
FIG. 6 shows a second example of embodiment also in a perspective sectional view, wherein only a portion of the housing is cut away, in a second end position.

A second example of embodiment of the connecting element $10_2$ according to the invention is shown in the second end position in FIG. 6. As also in the first example of embodiment, the connecting piece 22 has been moved into the second end position by means of the pre-stressing element 38. Unlike the first example of embodiment, however, the connecting piece 22 is solidly connected to the fiber-optic light guide 20, so that the latter has also been moved along the longitudinal axis A and no longer projects out beyond the front surface 19 of the housing 12.

Figure 7:
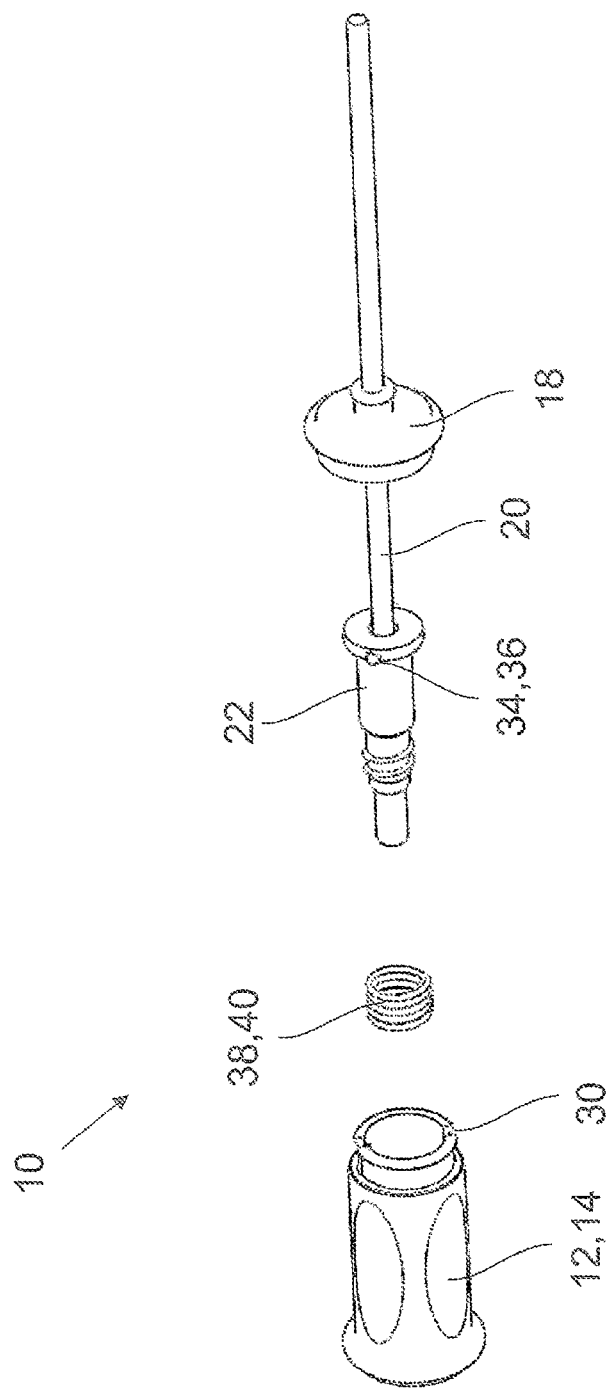
FIG. 7 shows the first example of embodiment in an exploded view.

The connecting element 10 according to the invention is shown in FIG. 7 on the basis of an exploded drawing. Since the first and the second embodiments differ only in the manner of how they are connected to the light guide 20, FIG. 7 shows the connecting element 10 according to the invention both according to the first embodiment as well as according to the second embodiment. There is recognized once more the housing 12, the pre-stressing element 38, the connecting piece 22 provided with the thread 24 and having the projection 36, and the cover 18, with which the housing 12 can be closed. The recess 30, in which the projection 36 can be introduced, can be recognized in housing 12. The fiber-optic light guide 20 in this case can be conducted through the housing 12.

Figure 8:
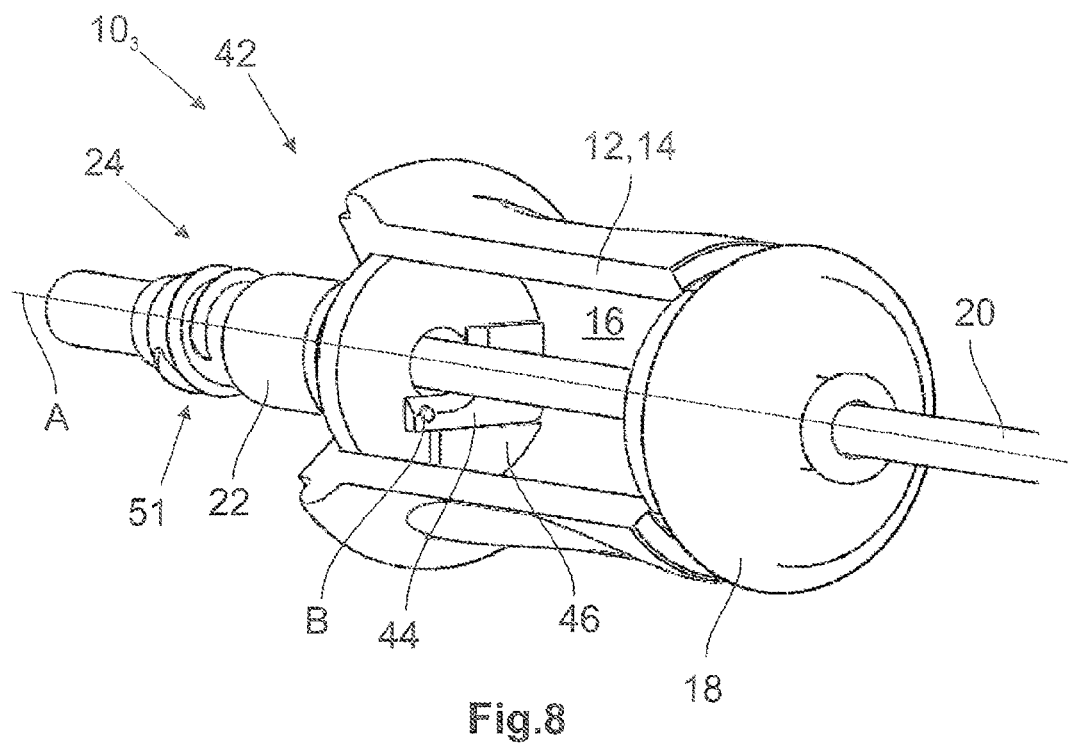
FIG. 8 shows a third example of embodiment in a perspective sectional view, wherein only a portion of the housing is cut away, in a first end position.
Figure 9:
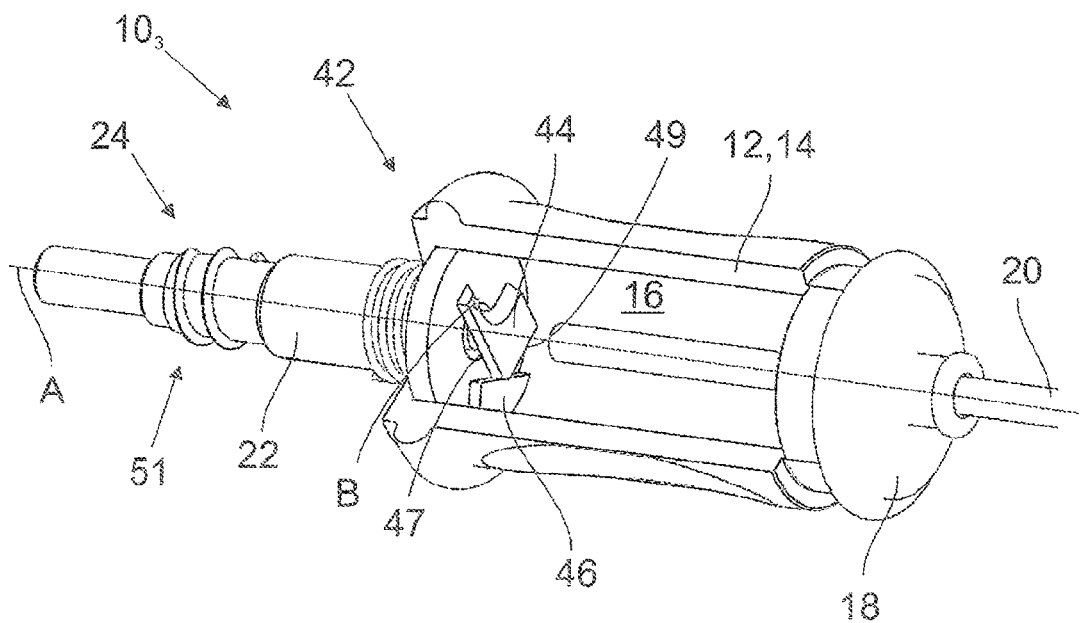
FIG. 9 shows the third example of embodiment in a perspective sectional view, wherein only a portion of the housing is cut away, in a second end position.

A third example of embodiment of the connecting element 10 according to the invention based on a perspective view is shown in FIGS. 8 and 9 in a first end position. The connecting element $10_3$ according to the third example of embodiment has a cutting element 44, which is rotatably mounted on the connecting piece 22 around an axis B. The connecting piece 22 itself is mounted rotatably in the housing 12, the housing 12 having a support section 46 on which the cutting element 44 is supported. The cutting element 44 has a first resting face 47 and a second resting face 49. When the connecting piece 22 is rotated into the connecting segment 28 by rotating the housing 12 in the screwing-in direction, no relative movement occurs between the connecting piece 22 and the housing 12, since the cutting element 44 rests by the first resting face 47 on the support section 46 and thus entrains the connecting piece 22. Now, if the housing 12 is rotated opposite to this in order to detach the connecting element 10 from the light source 26, there is a rotation of the housing 12 relative to the connecting piece 22, since first the friction between the thread 24 and the connecting segment 28 of the light source 26 must be surmounted and the connecting piece 22 remains. The cutting element 44 is shaped so that at first it does not entrain the connecting piece 22, if the housing 12 is rotated against the screwing-in direction. In order to increase the friction between the thread 24 and the connecting segment 28, the thread 24 can be provided with friction-enhancing means 51, for example, a coating or a roughened surface. The friction-enhancing means 51 can be designed so that screwing in is accomplished relatively easily, while in contrast, unscrewing is difficult, so as to give the user feedback of whether he is screwing in the light guide or is unscrewing it. In this way, the cutting element 44 is moved so that it severs the fiber-optic light guide 20 at least partially, as is shown in FIG. 9. Consequently, no light or only a greatly reduced quantity of light from the light source 26 can be guided through the fiber-optic light guide 20, so that it no longer can be used in a functionally correct manner and must be changed for a new one. Although only one cutting element 44 has been shown here, the invention is not limited only to the use of one cutting element 44. Of course, two, three or even more cutting elements 44 can be used, as long as this is appropriate. The B axis and the first and second resting faces 47, 49 of the cutting element 44 are configured so that with increasing relative rotation between the housing 12 and the connecting piece 22, the force necessary for this purpose is continually greater. Then, at the latest, when the second resting face 49 completely rests on the support section 46, a relative movement between the housing 12 and the connecting piece 22 is no longer possible. Then the connecting piece 22 follows the rotational movement of the housing 12 and the connecting piece 22 is removed from the connecting segment 28. At this point, however, the cutting element 44 has already completely severed the fiber-optic light guide 20.

Figure 10:
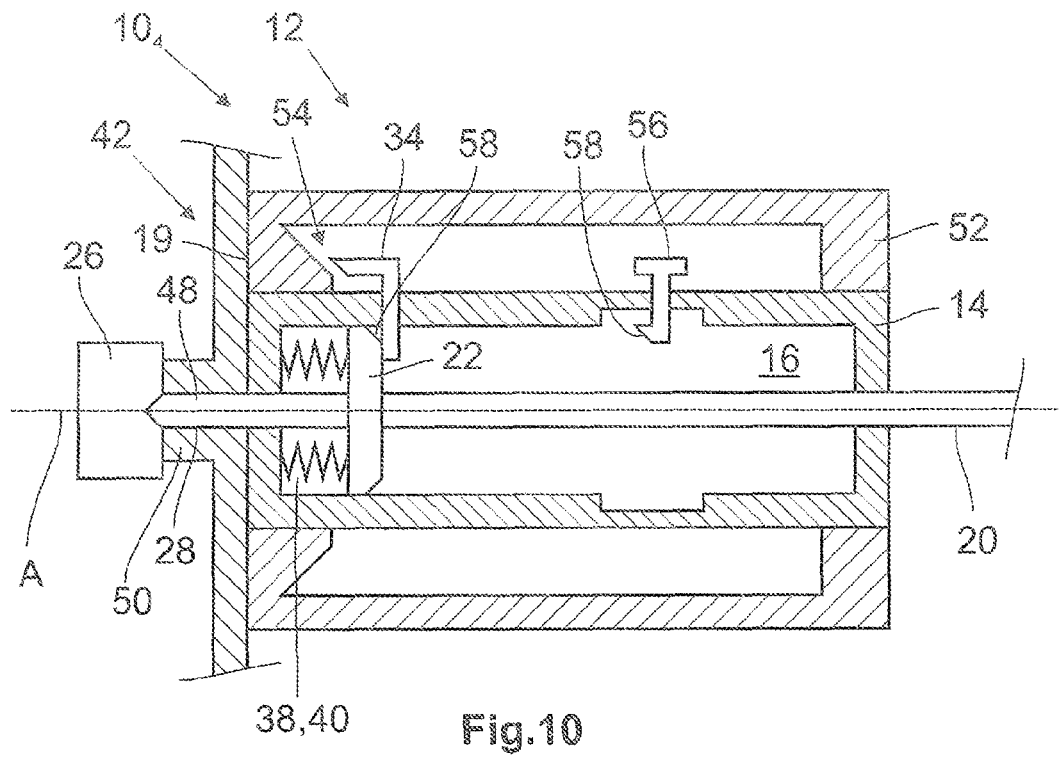
FIG. 10 shows a fourth example of embodiment of the connecting element according to the invention in a sectional view in a first end position.
Figure 11:
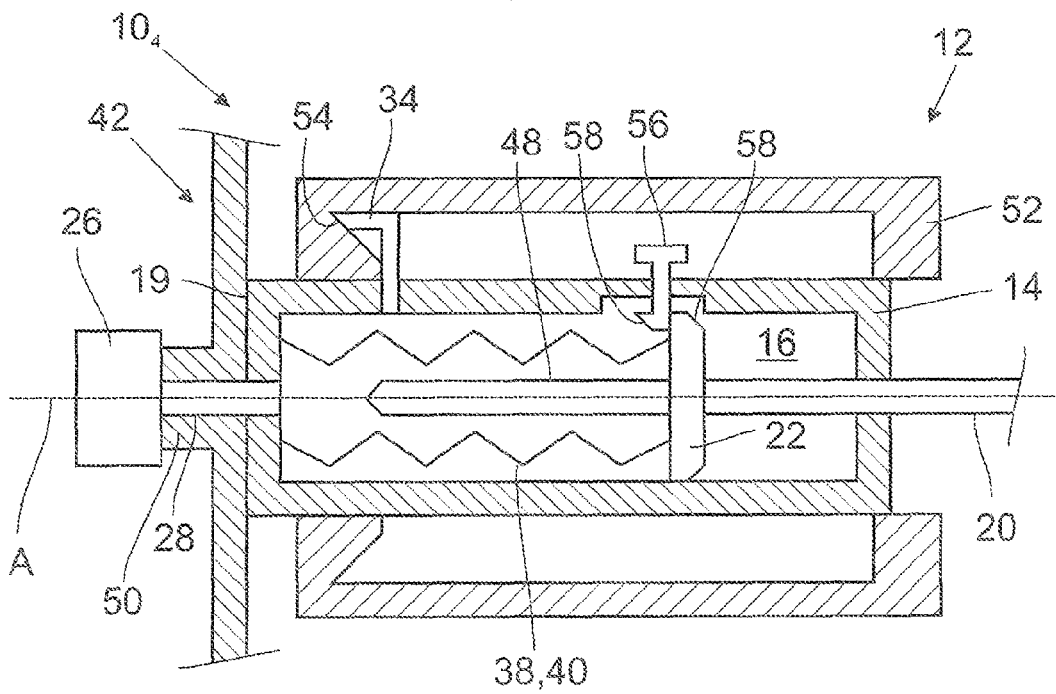
FIG. 11 shows the connecting element shown in FIG. 10 in a second end position.

A fourth example of embodiment of the connecting element $10_4$ according to the invention is shown based on a diagram of the principle in FIGS. 10 and 11. In this case, the connecting piece 22 is designed as a plug 48 (without thread), by which it can be connected to the light source 26 in the first end position, which is shown in FIG. 10. The light source 26 has a wall section 50, in which the connecting segment 28 that corresponds to the connecting piece 22 is disposed. It is recognized that the connecting piece 22 is held by the retaining element 34 in the first position, whereby the pre-stressing element 38 is pre-stressed. The housing 12 has a casing 52, which encloses the wall structure 14 of the housing 12 in a radially outward position, and which can be moved axially on the wall structure 14.

If the connecting element $10_4$ should be detached from the wall segment 50 of the light source 26, then a user grasps the connecting element $10_4$ by the casing 52 and pulls it away from the light source 26 essentially in the direction of the longitudinal axis A. In this way, the casing 52 moves in axial alignment, whereby the retaining element 34 is moved radially outward. For this purpose, both the casing 52 as well as the retaining element 34 have two conical segments 54. Due to the radial movement of the retaining element 34, the connecting piece 22 is released and, based on the pre-stressing force of the pre-stressing element 38, is moved axially into the second end position, in which the connecting piece 22 is completely disposed in the cavity 16. When moving from the first end position into the second end position, the connecting piece 22 moves a restraining element 56 axially outward. Both the connecting piece 22 as well as the restraining element 56 have conical regions 58, which point toward one another, if the connecting piece 22 is found in the first end position. Due to the contact of the conical regions 58, a radially outward directed movement of the restraining element 56 is induced. After the connecting piece 22 has passed the restraining element 56, and is found in the second end position, the restraining element 56 returns to its original position, for which reason restoring elements, for example, springs, which are not shown, can be provided. The conical regions 58 now no longer point toward one another, so that it is no longer possible to bring the connecting piece 22 from the second end position into the first end position.

Figure 12:
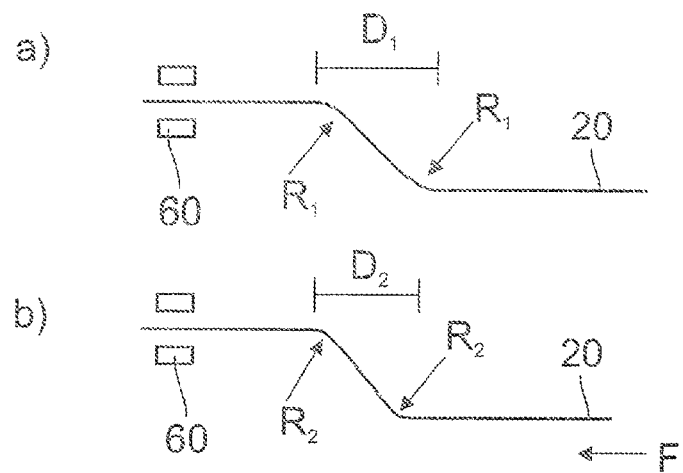
FIG. 12 shows a diagram of the principle of another possibility for using the connecting element according to the invention only once in a functionally correct manner.

Another possibility of how it can be achieved that the connecting element 10 can only be used once in a functionally correct manner is shown in FIGS. 12a) and 12b) based on a diagram of the principle. The fiber-optic light guide 20 is solidly clamped at a clamping site 60 and is bent at one or more places, so that it forms a corresponding number of radii $R_1$ (see FIG. 12a)). In the example shown, two radii $R_1$ are formed, which are disposed at a distance $D_1$. By introducing a force F in the direction of the clamping site 60, the distance is reduced to the measure $D_2$, whereby the radii are also reduced to the measure $R_2$. Each of the fibers used in the fiber-optic light guide 20 has a specific permissible bending radius, and when it is less than this, the fiber breaks. The radius $R_1$ is selected so that it lies above the permissible bending radius, whereas the radius $R_2$ lies below it. Therefore, at least a majority of the fibers will break, for which reason, only a fraction of the coupled light can be guided through the fiber-optic light guide 20. Each time depending on how the device employed by the user is equipped, a warning message is emitted, which makes noticeable the greatly reduced amount of light arriving at the distal end of the fiber-optic light guide 20, if the connecting element 10 should again be connected to the light source. An effective treatment is then no longer possible.

Figure 13:
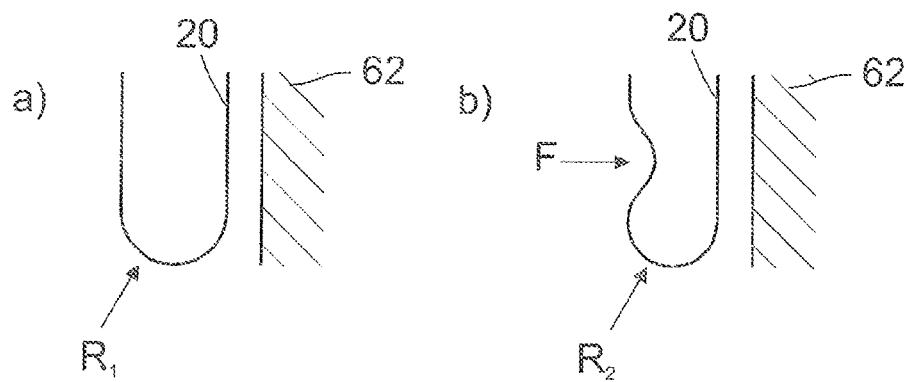
FIG. 13 shows a diagram of the principle of yet another possibility for using the connecting element according to the invention only once in a functionally correct manner.

The fiber-optic light guide 20 is also made into an arch structure in FIGS. 13a) and 13b), so that it passes through a radius $R_1$. Here, of course, the fiber-optic light guide 20 is bent by 180°, whereby a solid wall 62 runs on one side. In order to go below the permissible bending radius, a force F directed on the solid wall 62 is introduced onto the fiber-optic light guide 20, so that a radius $R_2$, which is smaller in comparison to $R_1$, is established (see FIG. 13b), which leads to the breaking of at least a majority of the fibers. The force F may be introduced, for example, by a wedge, which is moved parallel to the wall 62. Again, only a portion of the light can be guided through the fiber-optic light guide 20, which makes an effective treatment impossible.

The permissible bending radius amounts to approximately 60 times the diameter of the fiber, certain deviations being conceivable, for example, depending on the glass employed. For a fiber with a diameter of 70 μm, the permissible bending radius consequently amounts to approximately 4.2 mm. For many of the currently employed fiber-optic light guides 20, the permissible bending radius amounts to between 3 and 5 mm, which is determined experimentally in the so-called breaking-loop test.

Figure 14:
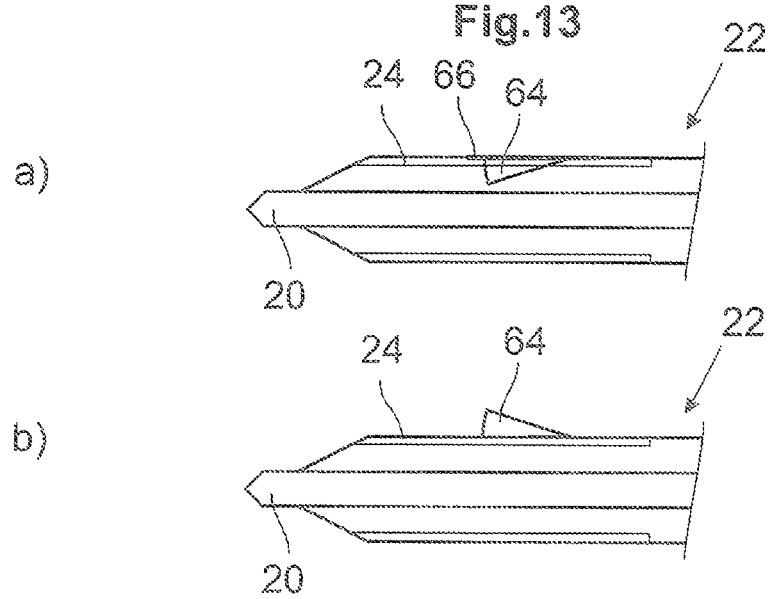
FIG. 14 shows an example of embodiment of a connecting piece according to the invention.

Another possibility of how the repeated use of the connecting element 10 according to the invention can be prevented is shown in FIGS. 14a) and 14b). Only a portion of the connecting piece 22, which comprises the thread 24, is shown in FIGS. 14a) and 14b). A pre-stressed thread segment 64, which is held in a first end position by a coating 66, a position in which it is completely integrated into the connecting piece 22, is disposed in the thread 24. In the first end position, the thread 24 can be screwed without problem into the connecting segment 28 of the light source 26. The coating 66 is selected so that it is abraded and/or destroyed based on the acting friction when it is screwed into the counter-thread of the connecting segment 28. Now, if the connecting piece 22 is again removed from the connecting segment 28, then the thread segment 64 is placed in the second end position by the pre-stressing force, as soon as the connecting piece 22 is no longer surrounded by the connecting segment 28 (FIG. 14b)). This movement represents a relative movement between the connecting piece 22 and the housing 12. A repeated screwing into the connecting segment 28 is then no longer possible. The thread segment 64 can be pre-stressed by pre-stressing elements such as springs; alternatively, the thread segment, however, can also be composed of elastic materials, which are compressed in the initial state and are thereby pre-stressed.

Figure 15:
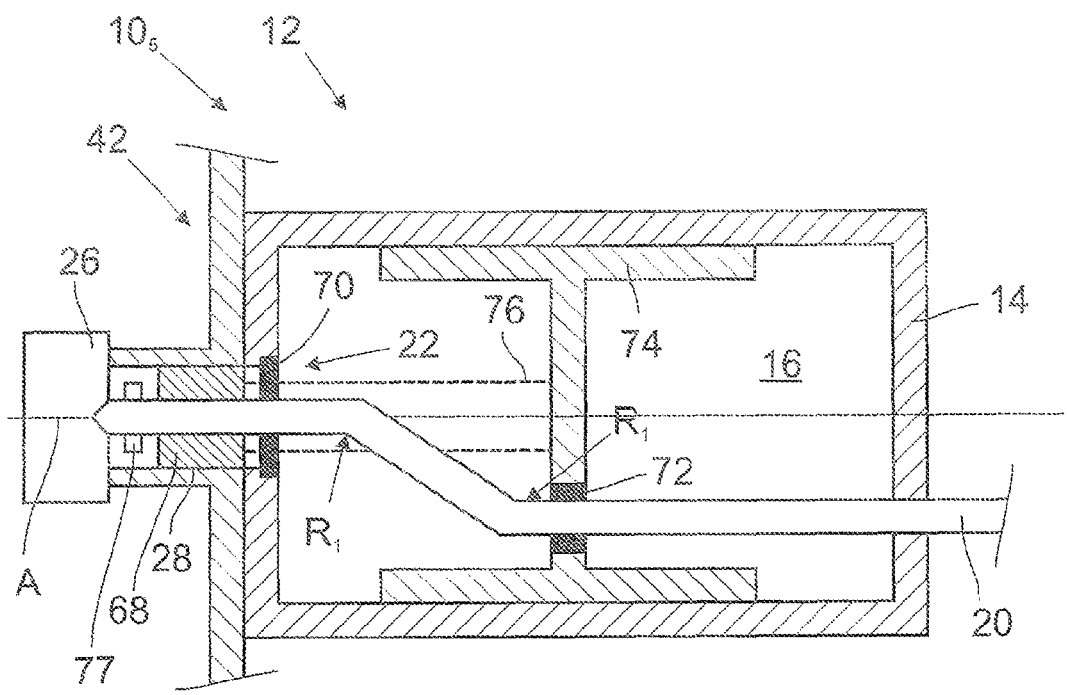
FIG. 15 shows a fifth example of embodiment of the connecting element according to the invention in a sectional view in a first end position.
Figure 16:
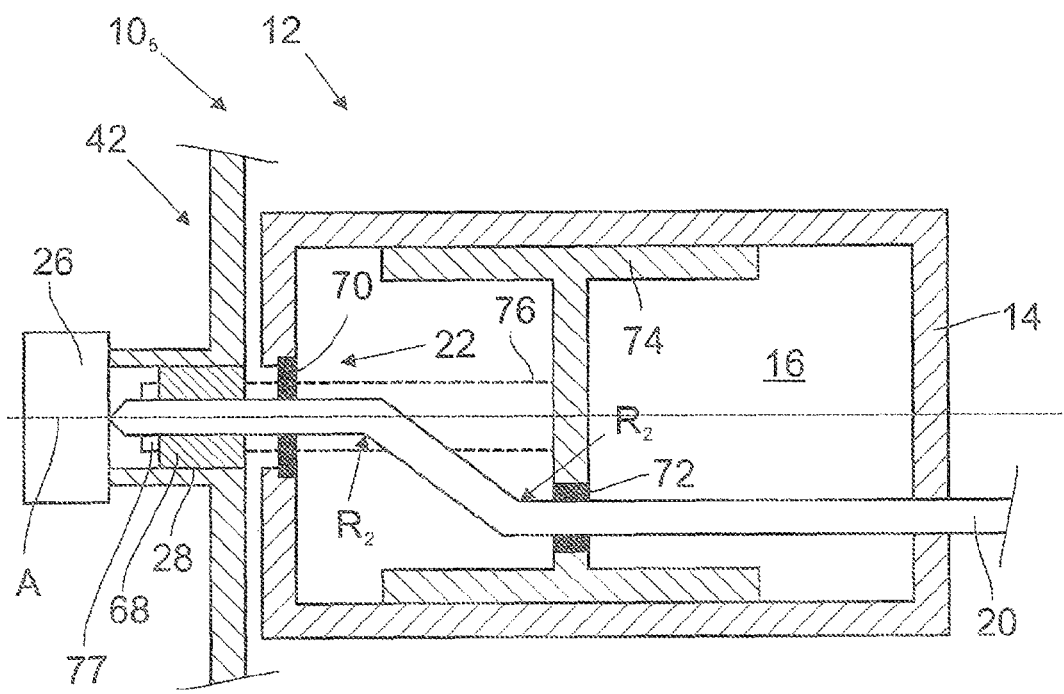
FIG. 16 shows the connecting element shown in FIG. 15 in a second end position.

Another embodiment of the connecting element $10_5$ according to the invention, which is based on a diagram of the principle that implements the principle shown in FIGS. 12a) and 12b), is shown in FIGS. 15 and 16. The connecting piece 22 comprises a casing piece 68, with which the fiber-optic light guide 20 is introduced into the connecting segment 28 of the light source 26. The casing piece 68 is introduced onto the fiber-optic light guide 20 so that it is relatively difficult to be able to move it onto the fiber-optic light guide 20 when the casing piece 68 is introduced into the connecting segment 28; however, when the casing piece is removed, it is relatively easy to be able to move it onto the fiber-optic light guide 20. The fiber-optic light guide 20 is solidly fixed by a first ring 70 to the wall structure 14 of the housing 12 approximately coaxially to the longitudinal axis A. The connecting piece 22 further has a tube element 74 that can be axially displaced in housing 12, the fiber-optic light guide 20 being fixed onto this tube element by a second ring 72, of course clearly eccentric to the longitudinal axis A. Consequently, the fiber-optic light guide 20 is bent so that it passes through two radii $R_1$. The tube element 74 is attached to the casing piece 68 by cords 76.

For connecting the fiber-optic light guide 20 to the light source 26, the casing piece 68 is introduced into the connecting segment 28 of the light source 26. In this case, a relative movement between the housing 12 and the connecting piece 22 does not occur. In order to separate the fiber-optic light guide 20 from the light source 26, the housing 12 is grasped and is removed from the light source 26 by a movement along the longitudinal axis A. The casing piece 68 in this case remains since it can be easily displaced on the fiber-optic light guide 20 in the connecting segment 28. The tube element 74 connected via the cords 76 to the casing piece 68 also remains stationary, so that the housing 12 is displaced relative to the connecting piece 22. Consequently, the distance between the first ring 70 and the second ring 72 is reduced, and the measure of the radii is reduced to $R_2$. In this way, the fiber-optic light guide 20 is bent beyond the maximum permissible measure, so that it is destroyed. Therefore, the casing piece 68 does not remain in the connecting segment 28, if an entrainment mechanism 77 is solidly attached to the fiber-optic light guide 20, which entrains the casing piece 68 when it is removed from the connecting segment.

Figure 17:
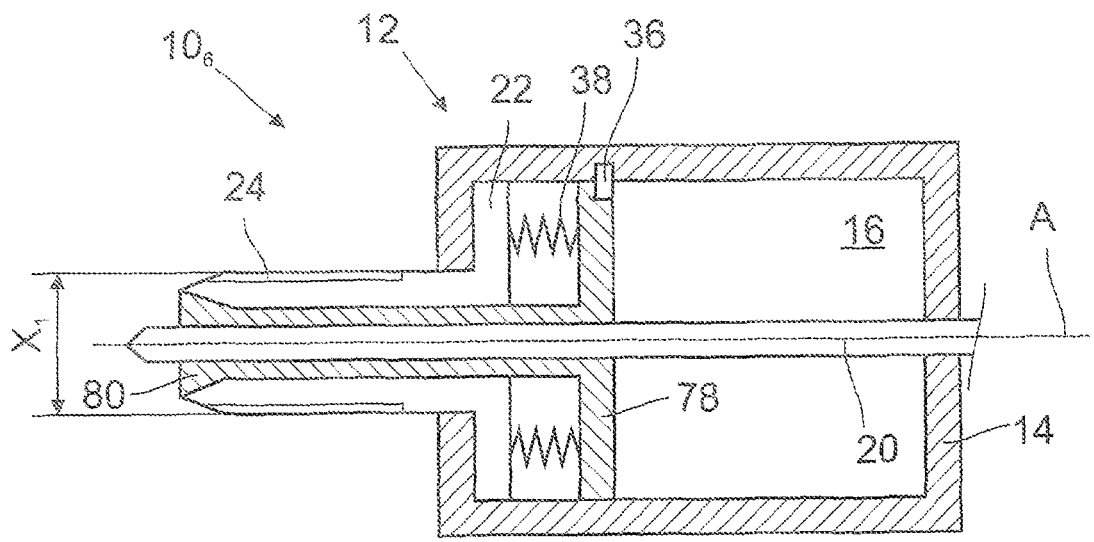
FIG. 17 shows a sixth example of embodiment of the connecting element according to the invention in a sectional view in a first end position.
Figure 18:
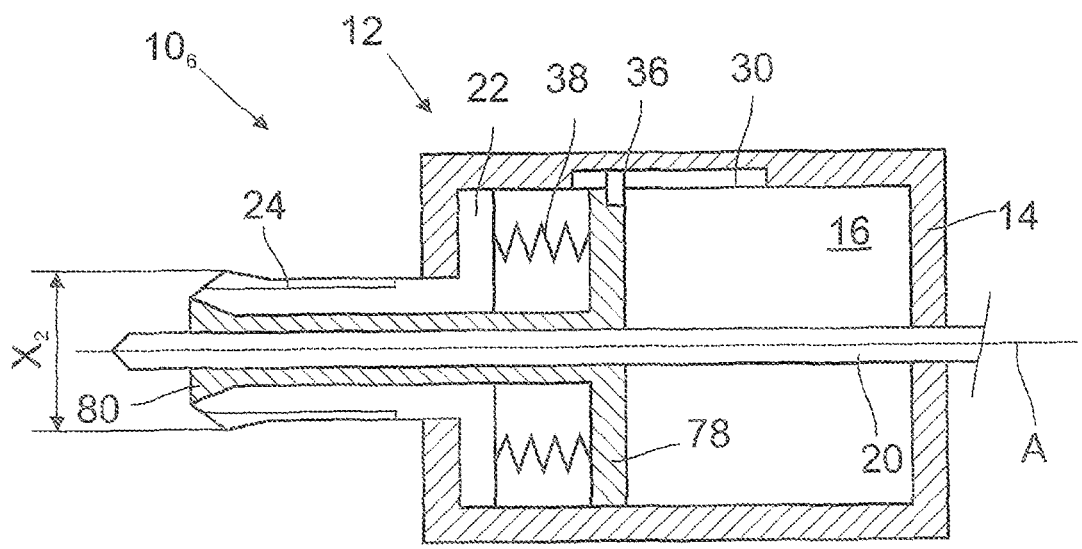
FIG. 18 shows the connecting element shown in FIG. 17 in a second end position.

Another embodiment of the connecting element $10_6$ according to the invention, which is based on a diagram of the principle, is shown in FIGS. 17 and 18. Here, a component 78, which is pre-stressed by the pre-stressing element 38 and which is disposed in a moveable manner on the fiber-optic light guide 20, passes through the thread 24 of the connecting piece 22. The component 78 has a conical end segment 80 and, analogously to the embodiment examples of the connecting elements $10_1$ and $10_2$, which are shown in FIGS. 1 to 6, is held by means of the projection 36 in a first end position, in which it is pre-stressed by the pre-stressing element 38. As long as the component 78 is found in the first end position, the thread has an outer diameter $X_1$. The thread 24 of the connecting piece 22 is now screwed into the connecting segment 28, which is not shown here, of the light source 26, for which reason the housing 12 is rotated in the screwing-in direction. When the housing 12 is unscrewed, it is rotated counter to the screwing-in direction, so that the projection 36 is placed in the recess 30, as is also the case in the first and second examples of embodiment $10_1$, $10_2$. The component 78 is now no longer held in the first end position and is moved by the pre-stressing element 38 into the second end position, which is disposed further removed from the thread 24. The material of the thread 24, the slope of the conical end segment 80 and the pre-stressing force provided by the pre-stressing element 38 are adapted to one another, so that the thread 24 is expanded radially outward to the diameter $X_2$ during the movement from the first end position in the direction of the second end position through the conical end segment 80 at a section surrounding the conical end segment 80 (see FIG. 18), so that a relative movement between the housing 12 and the connecting piece 22 occurs. In this way, the connecting piece 22 can no longer be screwed again into the connecting segment 28 of the light source 26, so that a repeated functionally correct use of the connecting element $10_6$ according to the invention is excluded.

LIST OF REFERENCE CHARACTERS

10, $10_1$-$10_6$ Connecting element
12 Housing
14 Wall structure
16 Cavity
18 Cover
19 Front wall
20 Fiber-optic light guide
21 Opening
22 Connecting piece
24 Thread
26 Light source
28 Connecting segment
30 Recess
32 Blocking segment
33 Closed end
34 Retaining element
35 Closed side wall
36 Projection
38 Pre-stressing element
40 Spring
42 Means or connection prevention device
44 Cutting element
46 Support section
47 First resting face
48 Plug
49 Second resting face
50 Wall segment
51 Friction-enhancing means
52 Casing
54 Conical segment
56 Restraining element
58 Conical region
60 Clamping site
62 Wall
64 Thread segment
66 Coating
68 Casing piece
70 First ring
72 Second ring
74 Tube element
76 Cord
77 Entrainment mechanism
78 Component
80 Conical segment
A Longitudinal axis
B Axis of rotation
D Distance
F Force
X Diameter

What is claimed is:
1. A connecting element for connecting a fiber-optic light guide to a light source one time and detaching the fiber-optic light guide from a light source one time, comprising:
a housing with a wall structure, which encloses a cavity;
a fiber-optic light guide passing through the housing and the cavity;
a connecting piece corresponding to a connecting segment of the light source for producing the connection with the light source, wherein the connecting piece is disposed at least partially in the cavity of the housing and encloses the fiber-optic light guide, wherein the connecting segment can be used again after detaching; and
a connection prevention device configured to prevent a repeated functionally-correct use of the connecting element and/or the light guide, the connection prevention device interacting with the connecting piece so that when the fiber-optic light guide is detached from the light source, the connecting piece can be moved into a second end position relative to the housing depending on one or more selectable events.

2. The connecting element according to claim 1, wherein the selectable event is a movement of the housing when the connecting element is connected to the light source or when the connecting element is detached from the light source.

3. The connecting element according to claim 2, wherein the connecting piece in the first end position projects out from the housing and the connecting piece is disposed completely or nearly completely in the cavity in the second end position, and wherein the connection prevention device comprises a pre-stressing element that pre-stresses the connecting piece in the first end position and a retaining element that holds the connecting piece in the first end position and releases the connecting piece based on the movement of the housing so that the connecting piece is moved into the second position by the pre-stressing element.

4. The connecting element according to claim 3, wherein the selectable event is a rotational movement of the housing.

5. The connecting element according to claim 4, wherein the retaining element comprises a projection that runs in a recess having a blocking segment.

6. The connecting element according to claim 3, wherein the selectable event is a translational movement of the housing so that the retaining element releases the connecting piece.

7. The connecting element according to claim 3, further comprising a restraining element configured to hold the connecting piece in the second end position.

8. The connecting element according to claim 1, wherein the connection prevention device is aligned so that with relative movement between the connecting piece and the housing, the fiber-optic light guide is moved so that the fiber-optic light guide falls below a permissible bending radius.

9. The connecting element according to claim 1, wherein the connecting piece has a thread that expands radially in the case of relative movement between the connecting piece and the housing.

10. The connecting element according to claim 1, wherein the connection prevention device comprises at least one cutting element for the at least partial severing of the fiber-optic light guide.

11. The connecting element according to claim 1, wherein the selectable event is the exceeding of a specific temperature.

12. The connecting element according to claim 1, wherein the selectable event is exposure to a specific dose of radiation.

13. The connecting element according to claim 1, wherein the fiber-optic light guide comprises a light guide selected from the group consisting of a quartz fiber, an individual glass fiber, a bundle of quartz fibers, a bundle of glass fibers, a plastic light guide, a liquid light guide, and combinations thereof.

14. The connecting element according to claim 1, wherein the connecting element is a fiber-optic component in a medical device used for the treatment of tissue surfaces.

15. The connecting element according to claim 1, wherein the connecting element is a fiber-optic component in a medical device used for surgical intervention with one of UV radiation, VIS radiation, and IR radiation.

16. The connecting element according to claim 1, wherein the connecting element is configured for use in a catheter.

17. The connecting element according to claim 1, wherein the connecting element is configured for use in a flexible-tubing usable in a medical treatment.

* * * * *